US009615795B2

(12) United States Patent
Kaku et al.

(10) Patent No.: US 9,615,795 B2
(45) Date of Patent: Apr. 11, 2017

(54) PROBE SUPPORT APPARATUS

(71) Applicant: CANON KABUSHIKI KAISHA, Tokyo (JP)

(72) Inventors: Wataru Kaku, Yokohama (JP); Sakiko Yamaguchi, Tokyo (JP); Shihoko Morota, Kawasaki (JP); Yoshiki Kuno, Tokyo (JP); Emi Nagamine, Tokyo (JP); Kazuhiro Watanabe, Tokyo (JP); Takeshi Nakata, Kawasaki (JP); Takahiro Noguchi, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 53 days.

(21) Appl. No.: 14/433,731

(22) PCT Filed: Oct. 8, 2013

(86) PCT No.: PCT/JP2013/005972
§ 371 (c)(1),
(2) Date: Apr. 6, 2015

(87) PCT Pub. No.: WO2014/068853
PCT Pub. Date: May 8, 2014

(65) Prior Publication Data
US 2015/0272502 A1 Oct. 1, 2015

(30) Foreign Application Priority Data

Oct. 29, 2012 (JP) ................. 2012-237939

(51) Int. Cl.
*A61B 5/00* (2006.01)
*A61B 8/00* (2006.01)

(52) U.S. Cl.
CPC .......... *A61B 5/6835* (2013.01); *A61B 5/0095* (2013.01); *A61B 8/4218* (2013.01); *A61B 8/4245* (2013.01); *A61B 8/4444* (2013.01)

(58) Field of Classification Search
CPC ... A61B 8/4218; A61B 8/4245; A61B 8/4444; A61B 5/6835; A61B 5/0095
See application file for complete search history.

(56) References Cited

U.S. PATENT DOCUMENTS 5,647,373 A * 7/1997 Paltieli ............... A61B 8/00
600/461
8,998,487 B2 4/2015 Watanabe et al. ........... 378/198
(Continued)

FOREIGN PATENT DOCUMENTS

| EP | 0654244 A1 | 5/1995 |
| JP | H04-210051 | 7/1992 |
| JP | 2005-312577 | 11/2005 |

*Primary Examiner* — Joseph M Santos Rodriguez
(74) *Attorney, Agent, or Firm* — Fitzpatrick, Cella, Harper & Scinto

(57) ABSTRACT

Employed is a probe support apparatus having: a base stand; an arm connected to an upper end of the base stand so that the arm can be tilted and rotated in a horizontal direction; and a probe support section connected to a distal end of the arm at a side opposite that of a portion connected to the base stand. The probe support section is constituted by a deformable section and a non-deformable section, and the non-deformable section is connected to a distal end of the arm so that the non-deformable section can rotate about an axis parallel to a rotation axis about which the arm is tilted.

9 Claims, 9 Drawing Sheets

(56) References Cited

U.S. PATENT DOCUMENTS

| | | | |
|---|---|---|---|
| 9,022,650 B2 | 5/2015 | Kaku et al. .................... | 378/197 |
| 2011/0021912 A1 | 1/2011 | Molnar ......................... | 600/439 |
| 2011/0201914 A1* | 8/2011 | Wang ................... | A61B 5/0059 |
| | | | 600/407 |
| 2011/0213247 A1 | 9/2011 | Shammas .................... | 600/437 |

* cited by examiner

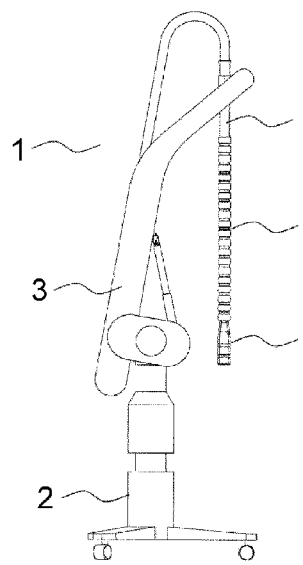 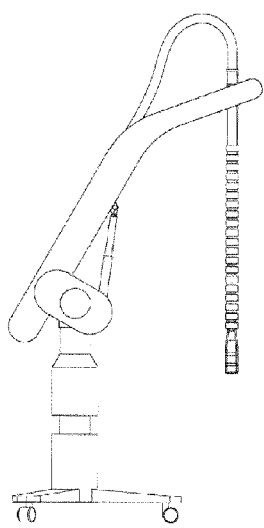 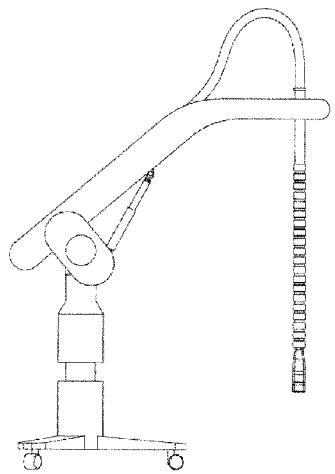
FIG. 6A   FIG. 6B   FIG. 6C
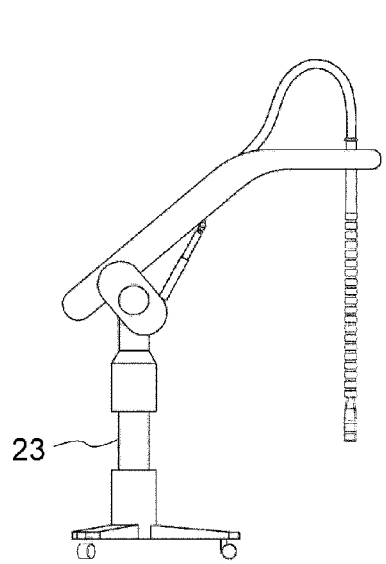 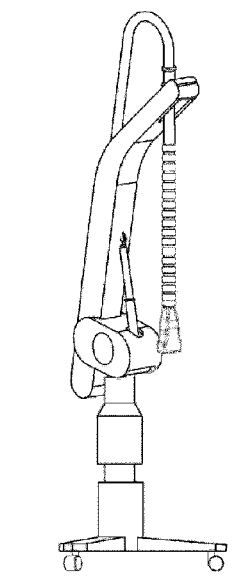
FIG. 6D   FIG. 6E

PROBE SUPPORT APPARATUS

TECHNICAL FIELD

The present invention relates to a probe support apparatus.

BACKGROUND ART

The examination with an ultrasound apparatus, more specifically a handheld ultrasound apparatus of a type such that the user holds an ultrasound probe in the hand, is performed by pressing the ultrasound probe connected by a cable to a main body to an examination segment. A probe support apparatus is known in which the cable is locked to a stand or an arm and the ultrasound probe is suspended from above in order to prevent the cable from coming into contact with the floor or the patient or hooking onto the bed during the examination.

Patent Literature 1 discloses a cable guide apparatus in which the cable of an ultrasound probe is incorporated in a foldable arm, and the ultrasound probe is suspended from the upper end of the arm. However, the problem associated with the cable guide apparatus disclosed in Patent Literature 1 is that the position of the arm should be adjusted in advance by manual operations according to usage state of the ultrasound probe, and the cable guide apparatus is difficult to operate.

Patent Literature 2 discloses an ultrasound apparatus in which the position of an ultrasound probe is specified with a sensor, and a cable support position at the upper end of an arm is controlled to be located vertically above the ultrasound probe, by a drive apparatus such as a motor. However, the problem associated with the ultrasound apparatus disclosed in Patent Literature 2 is that a sensor and a drive apparatus such as a motor are needed and the cost is increased.

Similar problems are also associated with a support for a photoacoustic probe in a photoacoustic apparatus for examination using the photoacoustic effect, such as described in Patent Literature 3.

CITATION LIST

Patent Literature

[PTL 1]
Japanese Patent Application Laid-Open No. H4-210051
[PTL 2]
Japanese Patent Application Laid-Open No. 2005-312577
[PTL 3]
US Patent Application Publication No. 2011/0201914

SUMMARY OF INVENTION

Technical Problem

The present invention has been created with consideration for the abovementioned problems, and it is an object of the present invention to provide a probe support apparatus that can support a probe so that the probe is positioned substantially directly above the examination segment.

Solution to Problem

The present invention provides a probe support apparatus comprising:

a base stand;
an arm connected to an upper end of the base stand so that the arm can be tilted and rotated in a horizontal direction; and
a probe support section connected to a distal end of the arm at a side opposite that of a portion connected to the base stand, wherein
the probe support section is constituted by a deformable section and a non-deformable section, and the non-deformable section is connected to a distal end of the arm so that the non-deformable section can rotate about an axis parallel to a rotation axis about which the arm is tilted.

Advantageous Effects of Invention

The present invention can provide a probe support apparatus that can support a probe so that the probe is positioned substantially directly above the examination segment, while inhibiting the increase in cost.

Further features of the present invention will become apparent from the following description of exemplary embodiments with reference to the attached drawings.

BRIEF DESCRIPTION OF DRAWINGS

FIGS. 6A to 6E illustrate the operation of the probe support apparatus of Example 3.

DESCRIPTION OF EMBODIMENTS

The preferred embodiments of the present invention will be explained below with reference to the drawings. The dimensions, materials, and shapes of the constituent components described hereinbelow, and mutual arrangement thereof should be changed, as appropriate, according to the configuration of the apparatus using the invention or various conditions, and the scope of the invention is not intended to be limited to the description below.

The probe support apparatus in accordance with the present invention can be used, for example, with an ultrasound probe for an ultrasound apparatus and a photoacoustic probe for a photoacoustic apparatus. In the ultrasound apparatus, an ultrasound wave is transmitted from an element inside the probe to the examination object, an echo wave reflected inside the examination object is received by the probe and information on the examination object is acquired as image data. In the photoacoustic apparatus, an acoustic wave (also called photoacoustic wave or photoultrasound wave) generated by a photoacoustic effect when the examination object is irradiated with light is received by the probe and information on the examination object is acquired as image data.

In the ultrasound apparatus, the acquired information on the examination object reflects the difference in acoustic impedance between the tissues inside the examination object. In the photoacoustic apparatus, the acquired information on the examination object is a distribution of generation sources of acoustic waves generated by light irradiation, an initial source pressure distribution inside the examination object or a light energy absorption density distribution and an absorption coefficient distribution derived from the initial sound pressure distribution, and a density distribution of the substance constituting the tissue. The density distribution of the substance as referred to herein is, for example, an oxygen saturation degree distribution or an oxidation-reduction hemoglobin density distribution. The acquisition of the information on the examination object can be realized by an information processing device by using a well-known reconstruction method on the basis of the reflected ultrasound wave or photoacoustic wave.

The probe types are not limited to those described hereinabove. The present invention is effective for supporting a handheld probe that is held and pressed by the user (for example, a health-care professional such as a laboratory technician and a doctor) against the examination object.

Example 1

Figure 1:
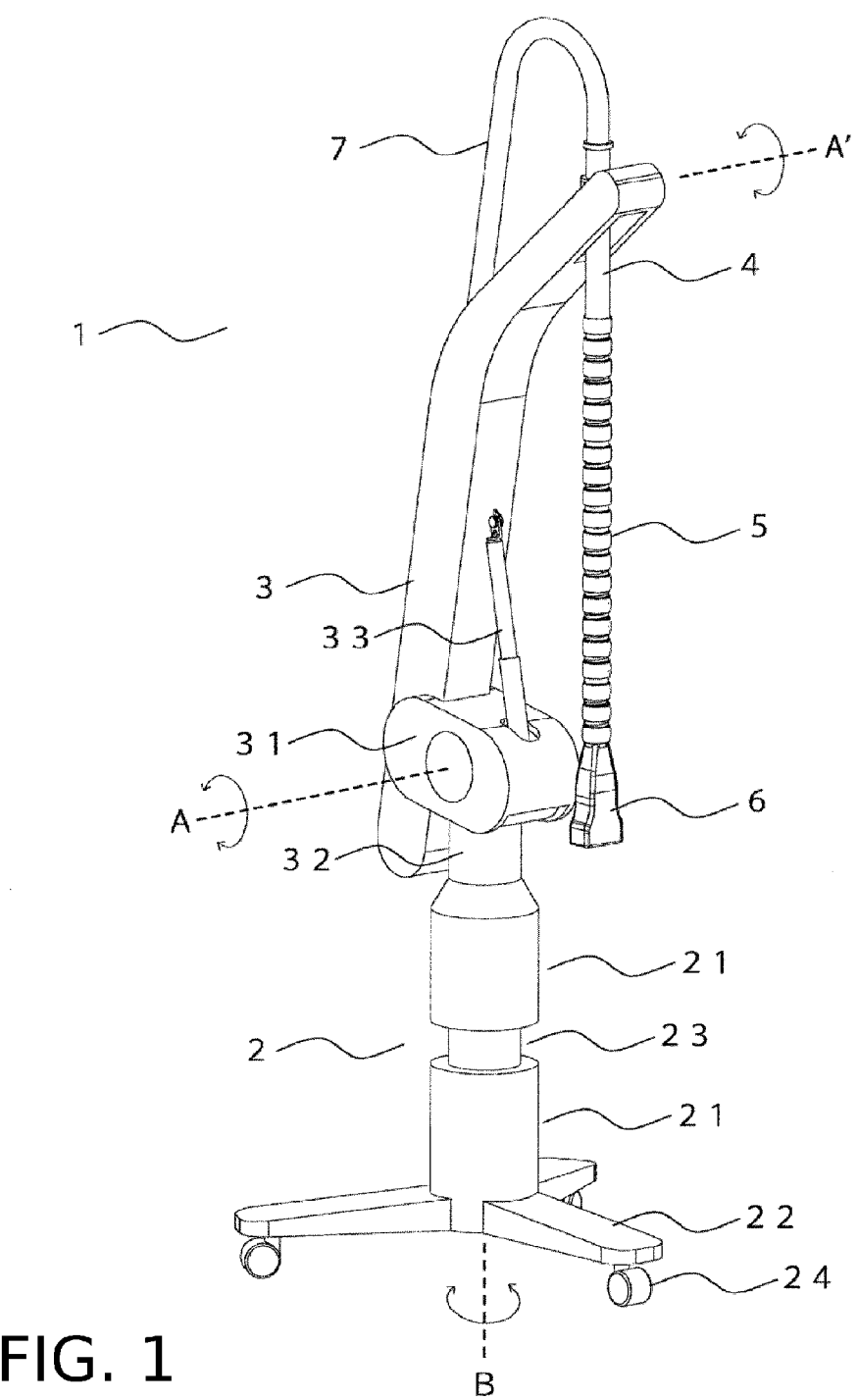
FIG. 1 illustrates the external appearance of the probe support apparatus of Example 1.

FIG. 1 illustrates the external appearance of the probe support apparatus of Example 1 of the present invention. A probe support apparatus 1 is mainly constituted by a base stand 2, an arm 3, a non-deformable section 4, and a deformable section 5. The non-deformable section 4 and the deformable section 5 can be together referred to as a probe support section.

The base stand 2 is a leg post supporting the entire probe support apparatus and is constituted by a columnar section 21 and leg blades 22. The height of the columnar section 21 can be changed by extension and contraction of a telescopic section 23. Therefore, the height of the probe support apparatus can be changed according to the height of the diagnostic table or the like. The leg blades 22 are configured in a branched form in the lower section of the base stand 2 and have a structure preventing the probe support apparatus from tumbling. Casters 24 are provided at the lower sections at the distal ends of the leg blades 22, and the probe support apparatus can be moved thereon. The lower section of the base stand 2 can also have a disk-shaped or rectangular structure instead of the leg blades 22.

The arm 3 is connected to the upper end of the base stand 2 so that the arm can be tilted and rotated. The tilting, as referred to herein, is the movement of the arm 3 in the tilting or lifting direction. This movement is realized by rotation about an axis A of a tilting-rotation section 31. The rotation in the horizontal direction is realized by rotation about an axis B of a horizontal rotation section 32.

The arm 3 is curved such that the distal end thereof protrudes in the tilting direction, thereby ensuring a space therebelow when the arm 3 is tilted. As a result, the user can easily perform the procedure and the patient does not get a feeling of pressure even in a tilted state of the arm 3.

The curved shape of the arm 3 is not limited to a dogleg shape as shown in FIG. 1 and can be a circular arc shape.

Concerning the tilting of the arm 3, the tilting angle of the arm 3 in the tilting direction is controlled to be maintained by a holding means 33 so as to prevent the arm 3 from tumbling under gravity. As a result, the arm 3 can be prevented from tumbling under gravity and the ultrasound probe can be prevented from hitting the patient. Further, since the arm 3 in a tilted state can be lifted by a smaller force, a burden on the user can be reduced. In the present example, the holding means 33 is constituted by a gas spring, but a mechanical spring, a counterweight, or a combination thereof can be also used.

The non-deformable section 4 is a cylindrical structural body that is connected in the vicinity of the upper end of the arm 3 so that the non-deformable section can rotate about an axis A' parallel to the rotation axis (axis A) about which the arm 3 is tilted. The non-deformable section 4 is part of the probe support section and connected to the distal end of the arm on the side opposite that of the portion of the arm connected to the base stand.

Figure 2:
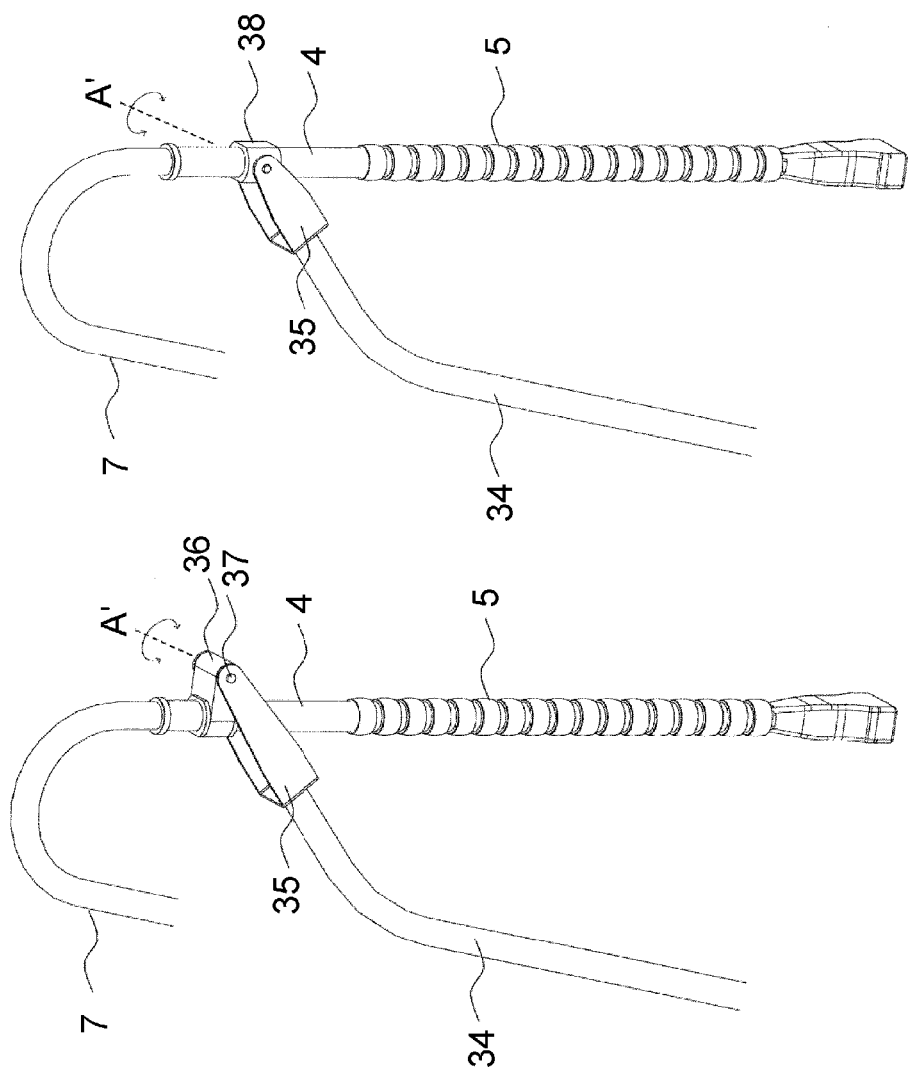
FIGS. 2A to 2C are outline drawings illustrating the connection section of the arm and the non-deformable section of the probe support apparatus of Example 1.

FIGS. 2A to 2C are outline drawings illustrating the connection section of the arm 3 and the non-deformable section 4 of the probe support apparatus of Example 1 of the present invention. FIGS. 2A to 2C show a state in which the outer frame of the arm 3 is removed and a frame 34 and a bearing 35 located inside are exposed.

As shown in FIG. 2A, the bearing 35 is connected to the upper end of the frame 34 configured inside the arm 3, and the bearing 35 is fixed so that a shaft 37 is inserted between two parallel metal plates thereof. A support body 36 is connected to be rotatable about the shaft 37, and the non-deformable section 4 is fixed so as to pass through the support body 36. The rotation of the support body 36 about the shaft 37 as the rotation axis is adjusted such that the non-deformable section 4 and the deformable section 5 hang down vertically under the weight of the non-deformable section 4 and the deformable section 5. As a result, the probe support apparatus 1 and the arm 3 can be moved such that the connection section of the arm 3 and the non-deformable section 4 are positioned directly above the examination segment, and user's operability is improved.

Concerning the connection section of the arm 3 and the non-deformable section 4, the two may be connected to enable rotation about the axis A' parallel to the rotation axis (axis A) about which the arm 3 is tilted. For example, a configuration can be used in which protrusions 39 configured integrally with the support body 38 are inserted in the bearing 35 as shown in FIGS. 2B and 2C. FIG. 2C is a view taken from above (top view) of the support body 38.

The deformable section 5 is a structural body that can be reversibly curved by applying a force thereto. The deformable section is connected to the lower end of the non-deformable section 4. In the present example, the deformable section 5 is constituted by a plastic cable guide. The cable guide is an outer shell member that accommodates inside thereof a power supply cable or a control cable of an electronic device and can prevent disconnection when the cable is moved. The deformable section 5 using the cable guide hangs down in the vertical direction when no external force is applied thereto, but is curved by a force applied to move the ultrasound probe 6 in the horizontal direction. Further, the deformable section 5 can transmit a force applied to lift the ultrasound probe 6 to the non-deformable section 4 and can lift the arm 3.

The member constituting the deformable section 5 is not limited to the cable guide, provided that this member can be curved reversibly and has a rigidity sufficient to transmit a force upward. Thus, an elastic body such as a rubber hose or a flexible arm constituted by a metal member such as stainless steel can be also used.

The ultrasound probe 6 is configured to include an element that emits and detects ultrasound waves for examination. A variety of such probes have been suggested correspondingly to the examination objects and segments. The ultrasound probe 6 may be a separate member that is connected to the probe support apparatus in accordance with the present invention or may be configured integrally with the probe support apparatus. In the former case, the probe can be replaced according to the examination object.

Figure 3:
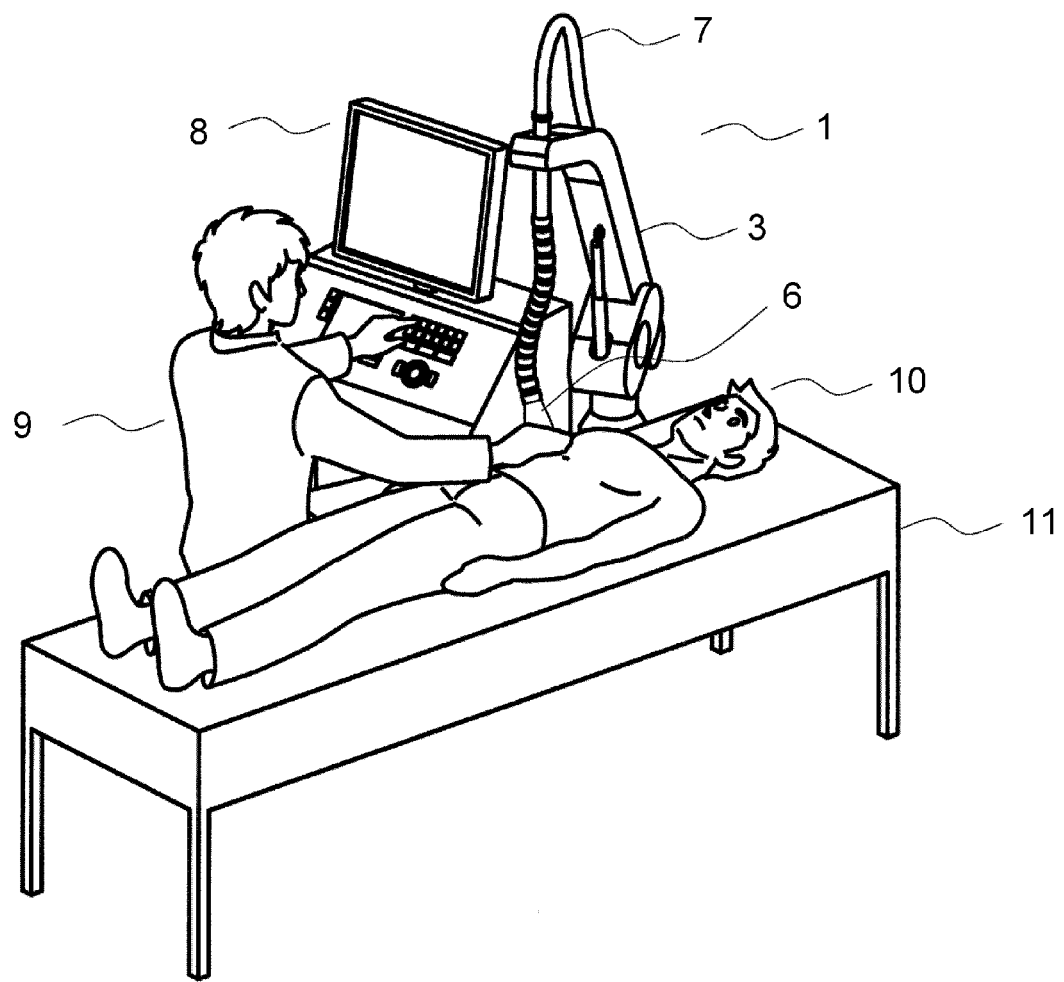
FIG. 3 is the usage state diagram of the probe support apparatus of Example 1.

FIG. 3 is the usage state diagram of the probe support apparatus of Example 1 of the present invention. The probe support apparatus 1 in accordance with the present invention is used in combination with the ultrasound apparatus 8 when ultrasound examination is performed. The ultrasound probe 6 is connected to the lower end of the deformable section 5, and the cable 7 is connected to the main body of the ultrasound apparatus 8 through the interior of the deformable section 5 and the non-deformable section 4. Thus, the ultrasound probe 6 is connected to the distal end of the deformable section 5 on the side opposite that connected to the non-deformable section 4. The user 9 adjusts the tilting and horizontal position of the arm 3 so that the ultrasound probe 6 hanging down from the arm 3 is positioned substantially directly above the examination segment of a patient 10 on a diagnostic table 11.

The user 9 then presses the ultrasound probe 6 held by the hand against the examination segment and performs ultrasound examination. When the measurement point is moved, the ultrasound probe 6 is moved, as is, toward a new measurement point, thereby applying a tension force to the shaft 37 through the deformable section 5 and the non-deformable section 4. Therefore, the arm 3 can be tilted and rotated in the horizontal direction. Where the examination is completed, the user 9 can lift up the ultrasound probe 6, thereby transmitting a force to the shaft 37 via the deformable section 5 and the non-deformable section 4 and moving the arm 3.

As explained hereinabove, with the probe support apparatus according to Example 1 of the present invention, the user can transmit a force to the arm and control the tilting and horizontal rotation of the arm 3, without using a drive device such as a motor. Therefore, the probe can be supported to be positioned substantially directly above the examination segment.

As a result, the ultrasound probe can be supported according to the usage state of the ultrasound probe, and a burden on the user can be reduced, while inhibiting the increase in cost.

By contrast with the probe support apparatuses disclosed in Patent Literature 1 and 2, since the cable 7 hangs down through the interior of the non-deformable section 4, no significant bending occurs in the vicinity of the upper end of the arm 3 and the probability of failure such as cable disconnection can be reduced.

Example 2

In Example 2, a probe support apparatus is explained in which the user lifts the arm by lifting through a distance equal to or greater than a predetermined value by using the rigidity of the probe support section (in particular, the deformable section).

FIGS. 4A to 4D are schematic views of a member constituting the deformable section of the probe support apparatus according to Example 2 of the present invention.

Figure 4A:
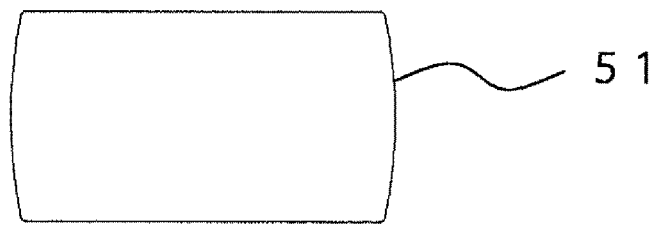
FIGS. 4A to 4D are outline drawings illustrating the members constituting the deformable section of the probe support apparatus of Example 2.
Figure 4B:
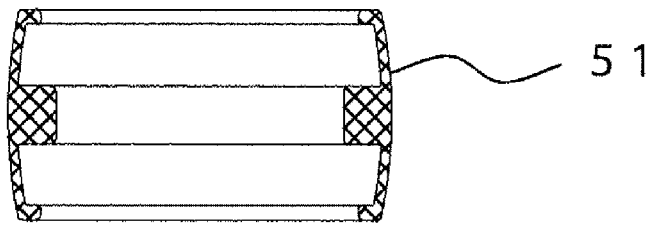
Figure 4C:
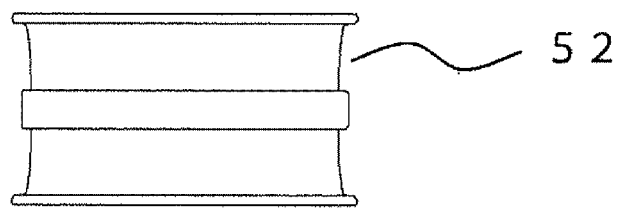
Figure 4D:
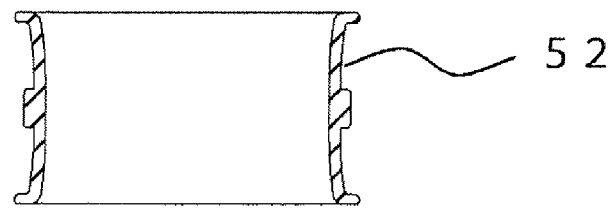

FIG. 4A is a side view of a member 51. FIG. 4B is a cross-sectional view of the member 51. FIG. 4C is a side view of the member 52. FIG. 4D is a cross-sectional view of the member 52.

In the present example, the deformable section 5 is configured by alternately connecting the members 51 and the members 52. The member 51 is a cylindrical structural body having an uneven shape on the inner wall, and the member 52 is a cylindrical structural body having an uneven shape on the outer wall. The diameter of the member 51 is slightly greater than the diameter of the member 52. Since the uneven shape of the inner wall of the member 51 and the uneven shape of the outer wall of the member 52 are designed to engage with each other, the members 51 and the members 52 can be connected.

Figure 5C:
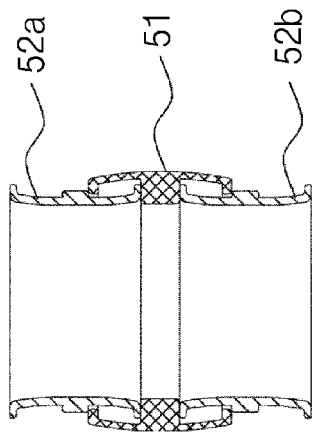
FIGS. 5A to 5C are schematic views illustrating the extension-contraction mode of the deformable section of the probe support apparatus of Example 2.
Figure 5B:
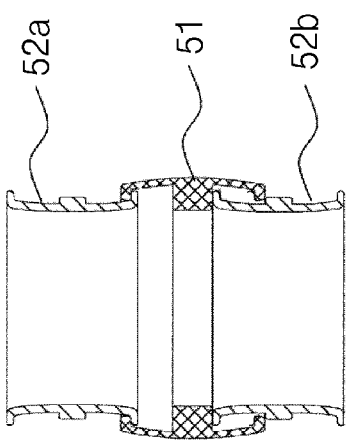
Figure 5A:
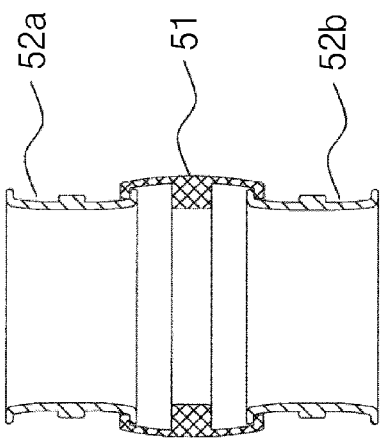

FIGS. 5A to 5C are schematic views illustrating the extension-contraction mode of the deformable section of the probe support apparatus according to Example 2 of the present invention. FIG. 5A shows a state in which the connection portion of the member 51 and the member 52 is extended. FIG. 5B shows an intermediate stage. FIG. 5C shows a contracted state.

FIG. 5A shows a state of the connection portion of the member 51 and the member 52 when a vertical downward force acts upon the deformable section 5, for example, when the deformable section 5 hangs down under gravity or when the user pulls the ultrasound probe vertically downward. In this state, the protruded portion at the upper end of the inner wall of the member 51 is caught in the protruded portion at the lower end of the outer wall of the member 52a, and the protruded portion at the upper end of the outer wall of the member 52b is caught in the protruded portion at the lower end of the inner wall of the member 51, whereby an extended state of the connection portion of the member 51 and the member 52 is obtained. Where an additional vertical downward force acts on the deformable section 5, for example, when the user pulls the ultrasound probe 6 further down in the vertical direction from this state, this force acts on the shaft 37 through a portion in which the protruded portions of the member 51 and the member 52 are caught in each other. As a result, the arm 3 is tilted downward.

FIG. 5B shows a state of the connection portion of the member 51 and the member 52 which is reached when the user slightly lifts up the ultrasound probe 6 in the vertical direction from the state shown in FIG. 5A. In this state, the member 52b located on the lowermost end of the deformable section is raised by the received force acting vertically upward, and the protruded portion at the upper end of the outer wall of the member 52b abuts against the protruded portion in the medium section of the inner wall of the member 51 connected on the upper side. Where the user further lifts up the ultrasound probe 6 vertically from this state, the member 52b at the lowermost end and the member 51 connected on the upper side are raised, while remaining in contact with each other, and the protruded portion of the medium section on the inner wall of the member 51 rises till it abuts against the protruded portion on the lower end of the outer wall of the member 52a connected on the upper side. As a result, a state is reached in which the connection portion of the member 51 and the member 52 is contracted, as shown in FIG. 5C.

The deformable section can be assumed to be connected in the order of the member 51, the member 52, ... also above the member 52a shown in FIGS. 5A to 5C. In this case, where a vertical upward force further acts in the state shown in FIG. 5C, the connection portions located above the member 51a successively, in the upward direction, reach the state shown in FIG. 5C. Where a force further acts vertically upward from the state in which all of the connection portions of the members 51 and members 52 have become such as shown in FIG. 5C, this force acts on the shaft 37 through the abutment portions of the protruded portions of the members 51 and the members 52. Therefore, the arm 3 is lifted.

As described hereinabove, with the probe support apparatus according to Example 2 of the present invention, even when the ultrasound probe is lifted, no force is transmitted to the arm before a predetermined distance is reached at which the connection portions of all of the members 51 and members 52 are contracted. Meanwhile, when the ultrasound probe is lifted through the predetermined distance at which the connection portions of all of the members 51 and members 52 are contracted, or through a greater distance, a force is transmitted to the arm and the arm is lifted. As a result, even when the user lifts the ultrasound probe within the predetermined distance to examine the vicinity of the examination segment, no force is transmitted to the arm and, therefore, the user can move the ultrasound probe by a light force. Meanwhile, when the user lifts the ultrasound probe through the predetermined distance or more in order to change the examination segment, a force is transmitted to the arm. Therefore, the probe support apparatus in accordance with Example 2 can support the ultrasound probe so that the probe is positioned directly above the examination segment, without using a drive device such as a motor, in the same manner as in Example 1.

The force that is equal to or smaller than a predetermined value and is thus absorbed by the deformable section 5 is not limited to the lift-up direction and may be in the horizontal or oblique direction. Thus, the deformable section 5 may use a material and have a structure such that when a force less than the predetermined value is applied thereto, this force is absorbed by deformations, and the transmission of a force to the arm is started only when a force equal to or greater than the predetermined value is applied thereto. Where the deformable section 5 is thus configured, difficulties associated with the overreaction of the arm to the user's operation can be avoided.

Example 3

Example 3 relates to the probe support device in accordance with the present invention in which the base stand extends or contracts according to the tilting of the arm.

FIGS. 6A to 6E illustrate the operation of the probe support apparatus of Example 3 of the present invention. FIG. 6A shows a state in which the arm 3 is lifted to the uppermost position, FIG. 6B shows an intermediate stage, and FIG. 6C shows the most tilted state of the arm 3.

Where the user pushes the arm 3 downward or pulls any of the non-deformable section 4, deformable section 5, and ultrasound probe 6 downward in the state shown in FIG. 6A, a downward force acts on the arm 3. As a result, the tilting-rotation section 31 of the arm 3 rotates about the axis A as a rotation axis, whereby the state shown in FIG. 6B is reached.

In the state shown in FIG. 6B, the arm 3 is prevented by the action of the holding means 33 from tilting under gravity, and even if the user's hand is withdrawn, the height is maintained. Where a downward force further acts from the state shown in FIG. 6B, the most tilted state is reached as shown in FIG. 6C. Conversely, where an upward force acts from the state shown in FIG. 6C, the arm 3 is lifted through the state shown in FIG. 6B to the state shown in FIG. 6A.

Where the arm 3 is tilted as is from the state shown in FIG. 6B to the state shown in FIG. 6C, the deformable section 5 and the ultrasound probe 6 can collide with the examination object of the diagnostic table. Accordingly, as shown in FIG. 6D, the telescopic section 23 extends following the tilting of the arm 3. As a result, the collision with the examination object or diagnostic table can be avoided. Further, where the arm 3 rises as is, the ultrasound probe 6 rises and can become unreachable by the user's hand. Accordingly, the position of the ultrasound probe 6 can be prevented from becoming too high by contracting the telescopic section 23 as the arm 3 rises. The extraction-contraction of the telescopic section 23 following the tilting of the arm 3 may be realized with the operation member, such as a foot pedal, operated by the user, or by providing a mechanism interlocking the extension and contraction with the tilting of the arm 3.

Where a force acts in the front direction from the state shown in FIG. 6A, the state shown in FIG. 6E is reached by rotation of the horizontal rotation section 32 in the front direction about the axis B as a rotation axis.

As described hereinabove, with the probe support apparatus according to Example 3 of the present invention, the user positions the ultrasound probe substantially directly above the examination segment by tilting the arm, without the danger of causing the collision of the probe with the patient or diagnostic table.

Example 4

Explained in Example 4 is a probe support apparatus according to Example 4 of the present invention which is configured to prevent bending to a predetermined angle or more.

In the deformable section 5 of the probe support apparatus in accordance with the present invention, bending to a predetermined angle or more can be prevented by using, for example, the following structure. In the present example, the deformable section 5 is configured by alternately connecting the members 51 and the members 52 in the same manner as in Example 2.

Figure 7A:
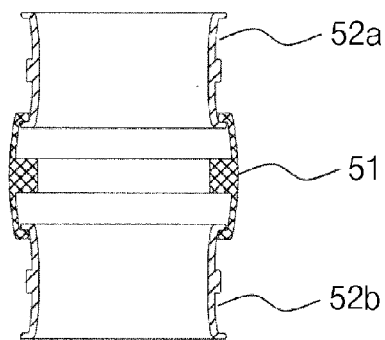
FIGS. 7A and 7B are schematic views illustrating the curving mode of the deformable section of the probe support apparatus of Example 4.
Figure 7B:
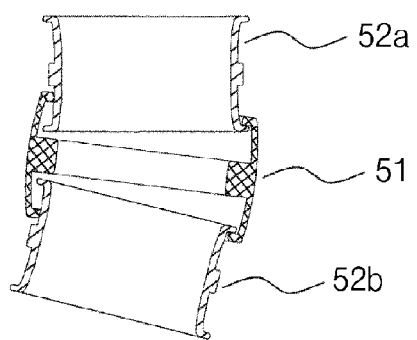

FIGS. 7A and 7B are schematic views illustrating the curving mode of the deformable section of the probe support apparatus according to Example 4 of the present invention. FIG. 7A shows the state in which the connection portion of the member 51 and the member 52 is extended linearly, and FIG. 7B shows the state in which the connection portion is curved by a force acting in the direction shown by an arrow.

Where the user tilts the ultrasound probe from the state shown in FIG. 7A and a force in a transverse direction or an oblique direction, with respect to the vertical direction, acts upon the deformable section 5, the member 51 and the member 52 are tilted in the connection portion therefor, and the curved state shown in FIG. 7B is reached. In the state shown in FIG. 7B, the protruded portion of the inner wall of the member 51 and the protruded portion of the outer wall of the member 52 abut against each other, and therefore the deformable section cannot be further curved. The angle at which the curving is restricted can be adjusted by changing the diameter of the members 51 and members 52, or the gaps between the protruded portions.

As described hereinabove, with the probe support apparatus of the present example, when a force acts in the direction inclined with respect to the vertical direction, the deformable section can be prevented from curving to a predetermined angle or more. As a result, it is possible to provide a probe support apparatus that can position the probe directly above the examination segment, while preventing the cable from damage caused by excessive bending.

Example 5

In Example 5, the probe support apparatus in accordance with the present invention is used with a photoacoustic probe for use in a photoacoustic apparatus. When a handheld photoacoustic probe is used, the probe should have a mechanism that irradiates the examination object with a pulsed light guided from a light source such as a laser, and a mechanism that detects a photoacoustic wave (typically, an ultrasound wave) generated from an absorbing matter in the examination object. Further, the ultrasound probe can be also imparted with the photoacoustic probe function by imparting the mechanism detecting the photoacoustic wave with the function of transmitting an ultrasound wave, or by providing a separate mechanism for transmitting an ultrasound wave.

Figure 8:
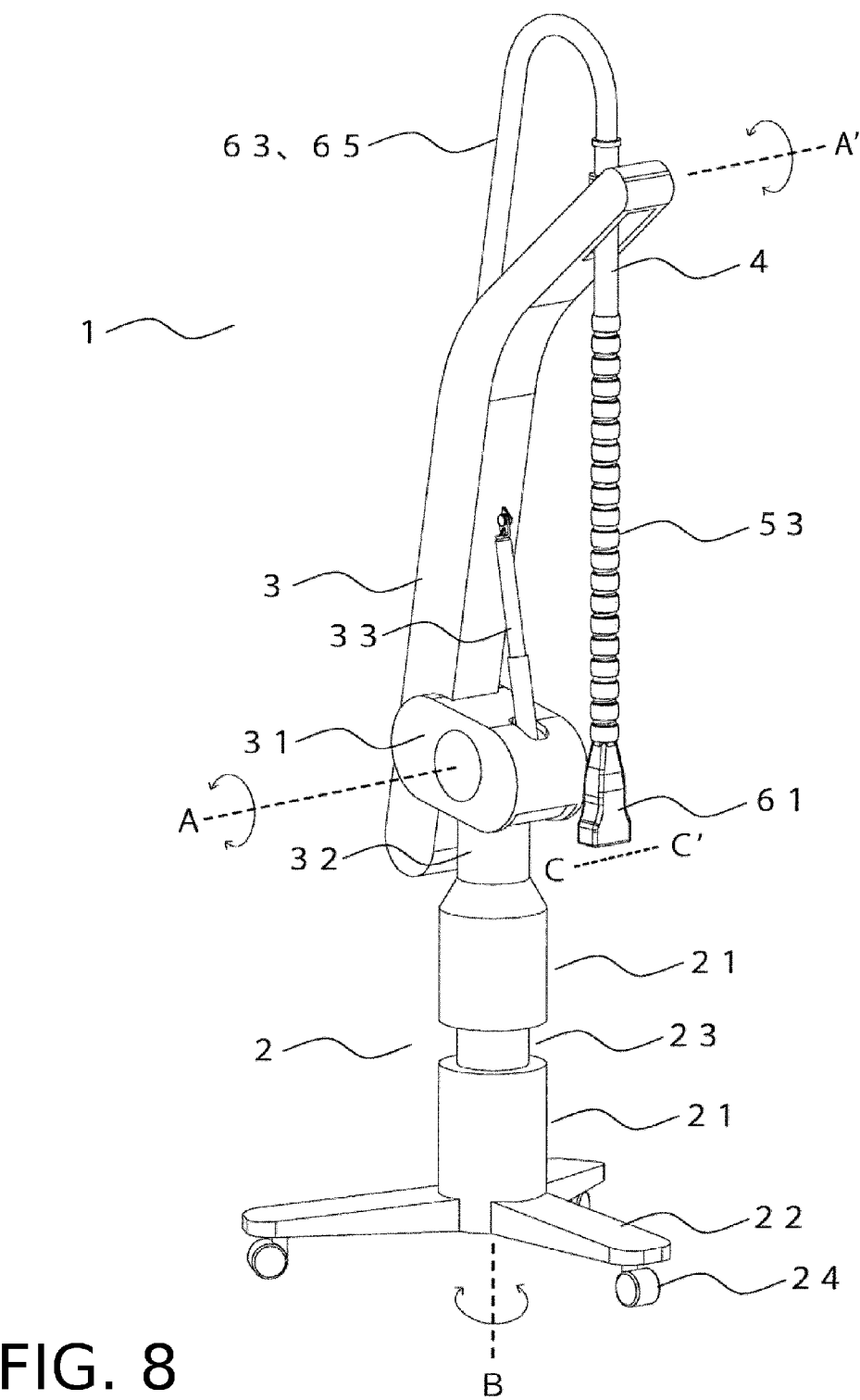
FIG. 8 illustrates the external appearance of the probe support apparatus of Example 5.

FIG. 8 illustrates the external appearance of the probe support apparatus according to Example 5 of the present invention. The components same as those in Example 1 are assigned with same reference numerals and the explanation thereof is herein omitted. A photoacoustic probe 61 is constituted by a unit (light irradiation unit) radiating pulsed light for performing photoacoustic examination and a unit (ultrasound unit) radiating and detecting ultrasound waves.

Figure 9:
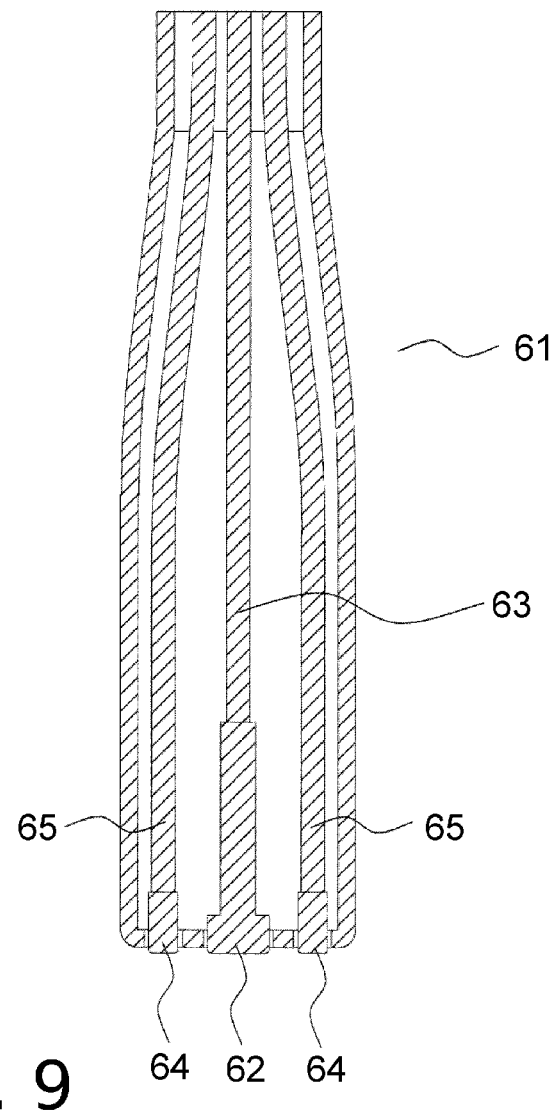
FIG. 9 is a cross-sectional view of the photoacoustic probe of Example 5.

FIG. 9 is a cross-sectional view of the photoacoustic probe 61 taken in a plane passing through points CC'. An ultrasound unit 62 includes an element that radiates and detects ultrasound waves and is configured similarly to the unit used in the ultrasound probe explained in Example 1. A cable 63 connects the ultrasound unit to the photoacoustic apparatus. A light irradiation unit 64 radiates pulsed light for photoacoustic examination and is configured by an optical prism for guiding the pulsed light emitted by the laser light sources to the examination segment. An optical fiber 65 is an optical member for guiding the pulsed light emitted by the laser light source to the light irradiation unit 64. Photoacoustic examination is realized by detecting with the ultrasound unit 62 the photoacoustic wave generated from the biological tissue under irradiation with the pulsed light radiated from the light irradiation unit 64.

A deformable section 53 is a structural body that can be reversibly curved by an external force and is similar to that explained in Example 4.

The photoacoustic probe 61 is connected to the lower end of the deformable section 53, and a cable 63 and an optical fiber 65 are connected to the photoacoustic device body through the interior of the deformable section 53 and the non-deformable section 4.

As described hereinabove, the photoacoustic probe is constituted by the light irradiation unit and the ultrasound unit. Therefore, the weight of such a probe becomes greater than those of probes that are generally used in the examination devices of this type. Further, since the probe support section is constituted by the cable transmitting electric signals and the optical fiber, this probe support section is more rigid than a typical probe support section. Further, since the optical fiber is an optical member guiding the pulsed light emitted by the laser light source, the performance thereof can be degraded by excessive bending. As described hereinabove, the probe support apparatus according to Example 5 of the present invention is particularly suitable, as a probe support apparatus useful for photoacoustic examination, for positioning the probe substantially directly above the examination segment.

In particular, where the configuration similar to that of Example 4 is used for the deformable section 53, the ability to follow the user's operation of the ultrasound probe can be maintained, while preventing excessive curving. Therefore, the probe support apparatus can be advantageously used with a photoacoustic probe using an optical fiber that needs high-level protection from bending.

Further, since the photoacoustic probe is heavy, the significant effect is that a burden on the user is reduced.

However, the configuration in accordance with the present invention can be used with all examination units having an examination probe.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-237939, filed on Oct. 29, 2012, which is hereby incorporated by reference herein in its entirety.

The invention claimed is:

1. A probe support apparatus comprising:
   a base stand;
   a horizontal rotation member having a circumferential rotation axis extending vertically, configured to rotate circumferentially with respect to said base stand and connected to said base stand;
   a tilting-rotation member having a tilt axis extending in a horizontal direction, configured to tilt with respect to said base stand and connected to said horizontal rotation member;
   an arm connected to said base stand via said horizontal rotation member and said tilting-rotation member so as to rotate circumferentially in a horizontal direction and tilt in a vertical plane; and
   a probe support member having a non-deformable section connected to said arm and a deformable section connected to said non-deformable section and configured to be connected to a probe,
   wherein said arm has an alternative tilt axis extending in said horizontal direction at a far side far from said tilting-rotation member, and
   wherein said non-deformable section is tiltably connected to the arm via said alternative tilt axis so that said non-deformable section can tilt around said alternative tilt axis parallel to said tilt axis.

2. The probe support apparatus according to claim 1, further comprising a probe connected to a distal end of said deformable section on a side opposite that of a portion connected to said non-deformable section.

3. The probe support apparatus according to claim 1, wherein said deformable section is in a state of hanging down in a vertical direction from a portion connected to said non-deformable section.

4. The probe support apparatus according to claim 2, wherein when a user lifts said probe through a distance equal to or greater than a predetermined value, said arm is lifted due to rigidity of said probe support member.

5. The probe support apparatus according to claim 1, wherein said probe support member transmits a force to said arm when a force equal to or greater than a predetermined value is applied thereto.

6. The probe support apparatus according to claim 1, wherein said base stand extends or contracts according to the tilting of said arm.

7. The probe support apparatus according to claim 1, wherein said deformable section has a structure such that bending at a predetermined angle or more is restricted.

8. The probe support apparatus according to claim 1, wherein the deformable section has an internal tubular space such that an electrical cable connected to the probe is inserted through.

9. The probe support apparatus according to claim 1, wherein the deformable section has an internal tubular space such that an optical fiber connected to the probe is inserted through.

* * * * *